United States Patent [19]

Cosman

[11] 4,411,266
[45] Oct. 25, 1983

[54] THERMOCOUPLE RADIO FREQUENCY LESION ELECTRODE

[76] Inventor: Eric R. Cosman, 872 Concord Ave., Belmont, Mass. 02178

[21] Appl. No.: 190,302

[22] Filed: Sep. 24, 1980

[51] Int. Cl.³ .............................................. A61B 17/39
[52] U.S. Cl. ............................... 128/303.18; 128/736
[58] Field of Search ........... 128/736, 784, 786, 303.18; 219/241

[56] References Cited

U.S. PATENT DOCUMENTS

| 3,698,394 | 10/1972 | Pier et al. | 128/784 |
| 4,108,163 | 8/1978 | Fleckenstein | 128/736 X |
| 4,204,549 | 5/1980 | Paglione | 128/784 |

FOREIGN PATENT DOCUMENTS 2407559  8/1975  Fed. Rep. of Germany ...... 128/804

Primary Examiner—Lee S. Cohen
Attorney, Agent, or Firm—Richard J. Birch

[57] ABSTRACT

A radio frequency (rf) lesion electrode design with a thermocouple temperature sensor in its distal uninsulated tip is described, having special design features which enable it to be made with very small tip diameters, flexible tip geometrics, very close proximity of the thermocouple sensor to the tissue the temperature of which must be measured, and very accurate and rapid temperature response. The two metal elements which are the two sides of the thermocouple junction, and the thermocouple junction itself are located in part on the external surface of the electrode's lesioning tip, essentially in direct physical contact with the tissue which is to be heated. This externalized sensor design is in contrast to all other temperature monitoring rf lesion electrodes to date where the sensors have been internalized, i.e., built inside the tip and not adjacent to heated tissue. The new design makes possible very small, sharpened-tip electrodes for micro surgical lesion procedures such as in making lesions in the spinal cord, i.e., cordotomies. Tip diameters of much less than 0.3 mm are practical, which is much smaller than previously achieved.

6 Claims, 9 Drawing Figures

THERMOCOUPLE RADIO FREQUENCY LESION ELECTRODE

BACKGROUND TO THE INVENTION

An rf (radio frequency) lesion electrode is a common instrument for use in neurosurgery. It typically consists of a metal conductor shaft which is insulated over its outer surface except for the surface of the electrode's distal tip. FIG. 1 represents such a shaft 1 with insulating coating 2. The tip of the electrode 1a is in conductive continuity with the shaft 1. Such a shaft is introduced into nervous tissue to a target which is to be destroyed by heat. This is done by attaching a radio frequency potential V form an rf source 3 through the metal shaft, thereby raising the tip 1a to rf potential. An indifferent electrode, or ground electrode, is usually attached to the patient's body at another location, thereby completing the current circuit from tip 1a to ground through the body of the patient. RF current eminating from the tip 1a will therefore ohmically heat the tissue around the tip, killing the tissue in a volume around the tip 1a which is raised above some critical temperature. Thus we achieve a kill-zone around the electrode's tip for the nervous tissue which surrounds the tip. The radius of the lesion or destruction zone depends on the radius of the electrode tip, on the temperature to which the tissue around the tip is raised, and on the physiologic nature of the nervous tissue which surrounds the tip. In this way localized destruction of tissue deep inside the brain, or other nervous structures such as the spinal cord can be achieved. This destruction often relieves pain and other nervous disorders in a dramatic, relatively non-evasive, way.

Because temperature is the basic lesioning or destruction parameter, temperature control or monitoring of the electrode's tip has become an essential means for carefully grading the degree of destruction and quantifying the lesion size. A rapid and faithful readout of tissue temperature just outside the tip is often critical to safety and successful results. Temperature monitoring lesion electrodes have existed since the early 1960's. They have all involved an internally located temperature sensor, illustrated by element 4 in FIG. 1, i.e., the sensor has always been placed inside the electrodes tip. Usually the shaft and tip, elements 1 and 1a in FIG. 1, are hermetically sealed stainless steel. Temperature sensor 4 is usually of either a thermistor or a thermocouple type, but other types are also possible. In the case that a thermistor is used, a pair of lead wires 5 and 5a must be brought out to the hub of the electrode 6 through electric contacts 5 prime and 5a prime. These, in turn, are connected to a temperature measuring circuit 7 which reads out the temperature. A cable would connect 7 to pins 5' and 5a'. A third pin 5a might be the contact for the rf source 3 to the conductive steel shaft 1. Sensing element 4 of FIG. 1 has also been of a thermocouple sensor type. Important performance criteria for the critical temperature measuring means is that it be accurate and fast-responding. Very often a fraction of a degree can mean the differernce between desired and unwanted differential tissue destruction. Speed of response can mean the difference between detecting a boiling or charring condition and not. Therefore, intimate thermal contact of the sensor 4 with the tip 1a is essential to improve these characteristics.

Typical rf lesioning electrodes run between diameters of 0.3 mm and 0.7 mm for lesioning in the brain. Lesioning in smaller neural-structures, such as the spinal cord, requires commensurately smaller electrode size. Temperature monitoring in the larger electrodes, roughly larger in size than 0.5 mm, has been relatively easy to achieve. Thermistors are available in small enough sizes and thermocouple junctions can be made small enough to allow such temperature sensors to be placed relatively easily inside tip geometries greater than about 0.5 mm in outer diameter. Furthermore for electrodes with tip diameters greater than about 0.5 mm, especially those with rounded hemispherical tips, as is used in brain lesioning, then inaccuracies due to non-uniform heating of the tissue are reduced. This is primarily because current densities for the larger electrode with smooth radii are relatively small, and thus tissue heating is rather uniform. This enables the tip to heat up in a uniform and average fashion, and permits the temperature sensor located within the tip to give a rather faithful representation of the overall tip temperature, and thus the surrounding tissue.

Severe technical problems, however, have been encountered in constructing electrodes less than tip diameters of about 0.5 mm with temperature sensors in their tip. Electrodes of 0.5 mm or less are essential for making lesions in the spinal cord, a procedure known as percutaneous cordotomy, which is a very common neurosurgical procedure and which has been performed for the last 20 years. All percutaneous cordotomy electrodes are less than 0.5 mm in diameter, and until very recently, all have been non-thermometric. The electrodes of Dr. Rosomoff, who initiated the technique, were 0.5 mm in diameter and had a tip length of 2.5 mm and a sharpened pointed tip. Dr. Mullan, also a pioneer in percutaneous cordotomy, used electrodes which were 0.25 mm in tip diameter with a 1.5 to 2 mm exposed tip length and also a sharpened pointed tip. The rf lesion electrodes that they used were solid stainless steel wires, and no temperature sensors were built into them. In fact, it was commonly believed, until recently, that temperature control for small electrodes of the cordotomy type could not be made on a commercial basis. The publications and advertisements of a major manufacturer of rf lesion generating systems and electrodes, the OWL Instrument Co., Limited of Canada, openly conceded that no manufacturer was able to make temperature monitoring percutaneous cordotomy electrodes because of the difficulties posed by the small size of the tip.

In the case of thermistor temperature sensors within the tip, the reason for the difficulty was clear. Thermistors have a finite size which are not easily available in dimensions of less than about 0.3 to 0.4 mm in diameter. Thus this poses an immediate limitation on the outer diameter shaft into which a thermistor can be installed. Thermocouple temperature sensors in principal do not have such a limitation since they only require the junction of two dissimilar metals. However, there are a variety of difficult technical problems in both fabricating such a thermocouple electrode and in making it suitable in accuracy and speed of thermometric response to be usable for very small-gauge rf lesion electrodes. These will be elaborated below after description of the construction of previous thermocouple rf lesion electrodes.

FIGS. 2A and 2B show the ways in which thermocouple rf lesion electrodes have been made by previous manufacturers. In FIG. 2A, a thermocouple rf cordotomy electrode made by Radionics, Inc. is shown. Wires 5a and 5b are dissimilar metals and their electrical junction 4 is the temperature sensing thermocouple junction. A variety of materials are possible for 5a and 5b such as: iron-constantan, copper-constantan, or other common thermocouple metal pairs. In this case, junction 4 is actually contacting electrically the metal stainless steel tip 1a on the interior surface of the tip. it is also possible to insulate 4 from 1a, but this reduces thermal conduction as well as speed and accuracy of temperature measurement. The electrode in FIG. 2A has a sharpened point on tip 1a for piercing the spinal cord, and this commercially available design, known as the TCE Thermocouple Cordotomy Electrode, and made by Radionics, Inc. is used in percutaneous cordotomies. Such an electrode has several technical problems. First, it becomes difficult to make the diameter of 1 below about 0.5 mm because the two insulated thermocouple wires must be placed within the tube 1. Second, the sensor 4 is not at the extreme tip end of the sharpened tip 1a, and this results in various sources of inaccuracies. For a sharpened point, the rf current density, and thus the tissue heating, is much greater at the very tip of the sharp point. Thus, the sharp point may be dangerously hot, even boiling, and the rest of tip 1a may be relatively cooler. Because the sensor 4 is placed internally in tip 1a, then it senses only the average tissue temperature around tip 1a, and this may be significantly below that at the very tip. Such a situation can produce dangerous inaccuracies in a critical procedure like cordotomies. Another inaccuracy arises from finite mass and heat conduction effects in the tip 1a itself. The metal tip of 1a takes a certain time to heat up when tissue at the sharp point end is raised quickly, as it often is when the tissue temperature is greater than 75° to 85° C. during typical cordotomies. The walls of tube 1 also conduct heat away at a finite rate, and this means that there is a temperature gradient between the very sharp end of tip 1a and the portion of 1a further back up the shaft, even in a thermal equilibrium or static thermal situation. Thus, the sensor 4, when not exactly at the surface of the sharp point end of 1a, will never be at the temperature of the hottest, most critical region near the very sharpest point of tip 1a. It is also true that when the sensor 4 is internal to tip 1a, and particularly when it is removed from the sharpest point of the surface tip 1a, then the sensor cannot respond as quickly as desirable to the rapid temperature changes taking place at the hottest region near the sharp point.

The above mentioned problems of thermal monitoring accuracy and speed of sensing response become relatively more important when the size of the electrode tip dimensions become smaller. The reasons for this are: (1) That, as the tip becomes smaller, the rf current densities become high for a given rf voltage, causing more unpredictable and variable spot-heating at the region of the electrodes tip; (2) For cordotomy electrodes, with a pointed tip and for which lesioning temperatures of 80° C. and up are common, the chance of unwanted runaway boiling at the tip becomes more of a problem, and faithful sensing response becomes critical to prevent disasterous damage to the patient. Often, the smaller the electrode, then the higher required tip temperature, and the more critical is the need for instantaneous temperature readout from the very tip end point; (3) As the diameter of shaft 1 becomes smaller, the larger is the ratio of the wall thickness of the shaft tubing and the diameter of the tubing. This results in great inaccuracies caused by heat flow losses up the shaft itself, i.e., the greater is the thermal gradient in the tip 1a itself, and, thus, the greater the difference between the pointed tip-end temperature and that at sensor 4.

There is a great need for temperature monitoring rf lesion electrodes of very small dimensions, viz. from about 0.5 mm to about 0.2 mm for cordotomies, and down to 0.1 mm or less for neurophysiolic research (<0.1 mm). The only such electrode, up to the time of the present invention, was the Type TCE Thermocouple Cordotomy Electrode System of Radionics, Inc., and that was of the design shown in FIG. 2A with a tip diameter of 0.5 mm. This was the situation despite the obvious need and the large number of cordotomies done around the world each year. This history is testimony to the difficulty in making a thermometric rf electrode of smaller size.

In passing, I note that, in FIG. 2A, the rf voltage source 3 activates the shaft 1, and thus the tip 1a. This voltage source is usually an externally located electronic circuit which attaches to the electrode via a cable. The temperature measuring circuit 7 is just a microammeter circuit for measuring the thermionic potential difference across the thermocouple junction 4. RF filter 8 blocks the rf voltage from 3 from getting into the delicate circuit 7.

Often in percutaneous cordotomies, the insulated lesion electrode telescopes through an uninsulated guide needle which serves as the return, or indifferent, electrode. Other voltages, such as for stimulation can be supplied to the electrode via the rf voltage connection. Also, electronic recording apparatus may be connected to the electrode prior or after rf lesion making. These techniques are standard and will not be elaborated in detail here.

It is worth noting, further, as background to this invention, that there has been only three other reported thermocouple rf lesion electrode systems. The system of VandenBerg, published in 1960 and commercialized as the Coagrader System by Vitatron in the same year, utilizes a thermocouple electrode design is shown in FIG. 2B. In it, the junction 4 is again internal to the tip 1a, and is made between the stainless steel tip material and the constantan metal wire 5. VandenBerg, et al shows a blunt-ended electrode of 2 mm tip diameter and 2 mm tip length, and the junction sensor 4 well inside the tip 1a. The objective of VandenBerg's electrode was for relatively large-volume lesion making in the brain, not for very small lesion making as required for example in the spinal cord. For the purposes of the very small electrodes, that is smaller than about 0.5 mm, VandenBerg, et al's electrode and internal sensor construction would be inadequate for the reasons cited above. Furthermore, the internalized thermocouple junction location, as shown by VandenBerg, is difficult to fabricate in small gauge electrodes. For sharp tip designs, as discussed above and used in cordotomy applications, VandenBerg's construction is especially disadvantageous since it accentuates the above cited problems. It might be noted that the Coagrader System and electrode of VandenBerg, et. al. survived only about four years on a commercial basis from about 1968 until 1972, suggesting the practical difficulties encountered by their system, as contrasted with the success of the Radionics and OWL systems.

The two other systems are: the Riechert-Mundinger Lesion Generator System as described by Mundinger et. al. and commercialized by F. L. Fischer; and the Leksell System. Both these systems utilized electrodes of the type shown in FIG. 2A, i.e. internalized thermocouple temperature sensors. It is notable also, that both of these systems offered only stereotaxic lesion electrodes for use in the brain, these electrodes having a minimum diameter of 1.8 mm. Of the five manufacturers or rf lesion electrodes and lesion generators, the companies OWL Instruments Ltd. Vitatron, F. L. Fischer, and Leksell never offered a thermometric cordotomy lesion electrode, and only the company Radionics, Inc. did offer such an electrode recently, but it was limited in size to greater than 0.5 mm in diameter, and in performance because it was of the design shown in FIG. 2A.

DESCRIPTION OF THE INVENTION

The present invention relates to a thermocouple rf lesion electrode construction design which overcomes the problems discussed above, and which enables commercially viable production of practical, accurate, and fast-acting electrode with very small tip dimensions, as is vitally needed in percutaneous cordotomies, other micro neurosurgical procedures, and neurophysiological research. The design has been used to produce a 0.25 mm diameter cordotomy electrode with sharpened tip, and use of this electrode in its first 20 clinical trials has recently been reported by Levin and Cosman.

Figure 1:
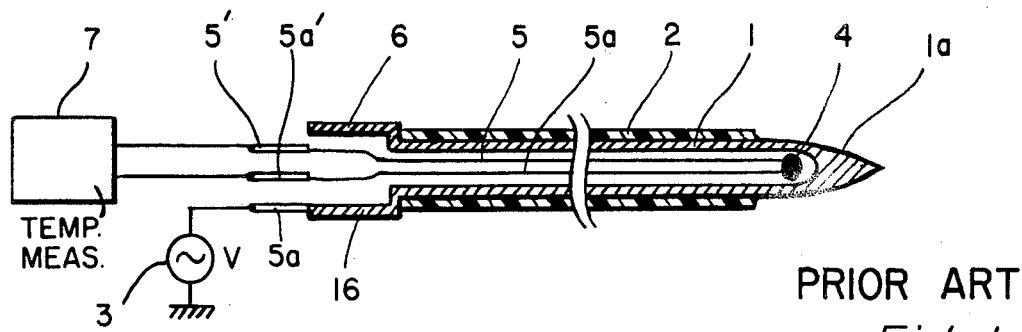
FIGS. 1 and 2A and 2B are views in partial section and block form of prior art of lesion electrodes.
Figure 2A:
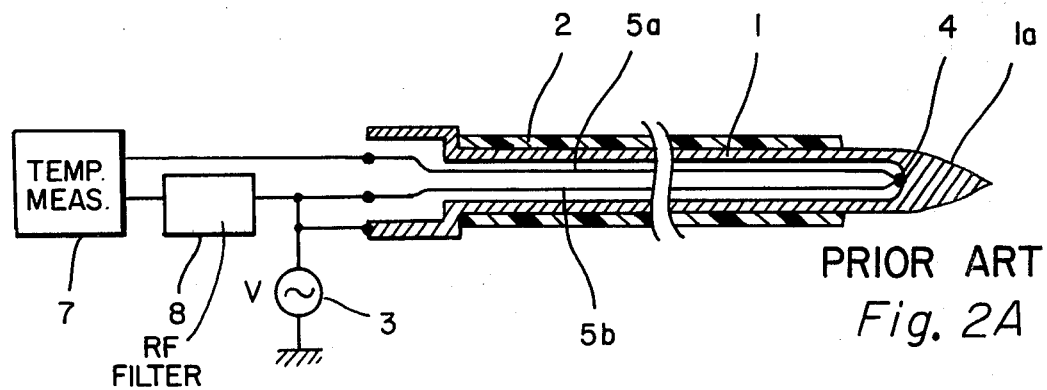

FIG. 3 illustrates sectional views of the new electrode design for a variety of embodiments which might be used in different mini or microelectrode applications. FIG. 3A again has a conductive metal tubular shaft 1 which is insulated by material 2 except for bare tip 1a. Inside 1 is another metal conductor element 5 which is insulated from 1 by material 9 except for a thermocouple junction 4 of metals 5 and 1 at the extreme sharp point of tip 1a. The junction is positioned and so made that portions 5" and 1" of conductors 5 and 1, respectively, are part of the external surface of the rf lesion tip 1a at the location of the junction 4. This might be referred to as an externalized thermocouple junction, in contrast to the internalized sensors illustrated above in FIGS. 1 and 2.

The advantages of this externalized thermal sensor are manifold. By having the two contacting thermocouple elements of the sensor 1" and 5" joined electrically at a point 4 which is in part a portion of the active rf surface 1a of the electrode, then the sensor is actually in contact physically with the adjacent tissue that is being heated. Since the junction 4 in FIG. 3A includes part of the external surface, then the junction potential generated across it is a close representation of the real temperature at the surface of the tip. This is very important for very small lesion electrodes such as for cordotomies, since for them the lesion temperatures are typically very high, even close to the boiling 100° C. point. For example, as noted by Levin and Cosman, who used the 0.25 mm electrode in many cordotomies, the tip is raised to 80° and 85° routinely to achieve a proper lesion. At that point, any non-uniform hot spots must be monitored to prevent runaway flash heating to the boiling point of 100° C.

Figure 3A:
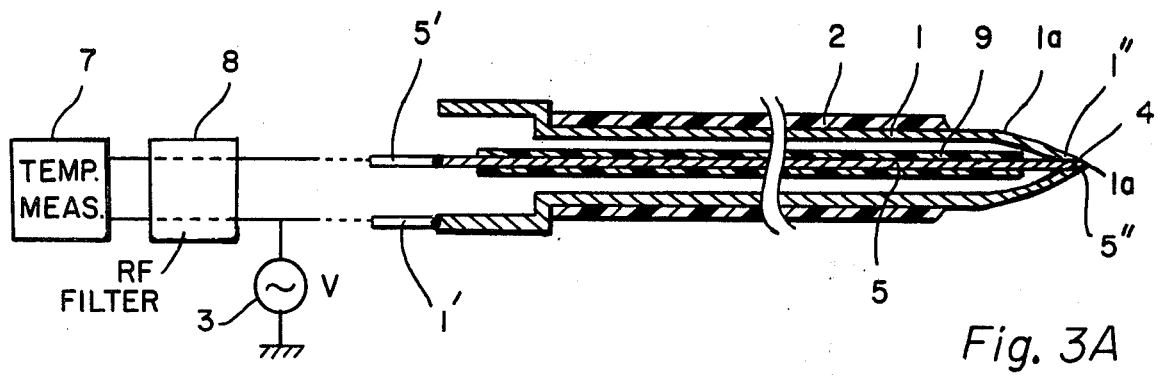
FIG. 3A is a comparable view in partial section and block form showing one embodiment of the invention; and, FIGS. 3B through 3F are views in partial section of the distal end portions of other embodiments of the lesion electrode of the present invention.

Another advantage of the externalized sensor in FIG. 3A, in contrast to previous internalized sensor constructions, is that the sensing junction 4 is located at the sharpest point of tip 1a; in fact, it is the very pointed end itself. This means that it is sensing the temperature where the heated tissue is hottest, i.e. where the rf current density is greatest. This is the first location that boiling or charring will occur, and thus, for safety reasons, it is the most important point to be monitored. That one is measuring the temperature of the hottest point, and not an average tip temperature, as is the case for internalized sensor designs, means that one has again a more faithful measure of the lesion process, and more control thereof.

Another advantage of the design of FIG. 3A is the fact that the mass of the sensor junction 4 is very small so that the speed of response is commensurately fast. The wall thickness and associated thermal conduction up the shaft makes no difference to the accuracy of the temperature readout, since there are no gradients between the tissue and the location of the sensor.

Yet another advantage of the design of FIG. 3A is the simplicity of its construction and its amenability to construction of very small diameter electrodes. The central metal element 5 is easily telescoped into a tube 1, and its end is easily welded or soldered to the tube at the tip end. The point may then be sharpened easily, if a point is desired. The junction 4 being external, means that its integrity is easily seen, compared to internalized designs. Electrodes of the type in FIG. 3A have already been made down to 0.1 mm diameter, and smaller ones are possible. Such sizes are difficult to make if one begins with a closed end tube, and then inserts a thermocouple wire pair down from the open end to the interior of the tip. Such an internalized design then has all the disadvantages cited above.

Figure 3B:
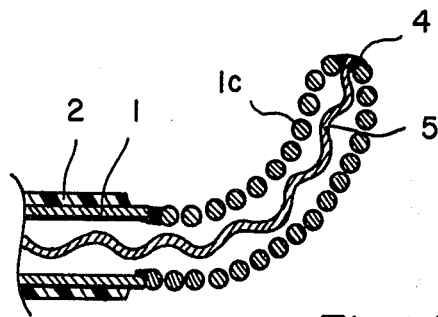

We note that tubing 1 is usually stainless steel, and wire 5 is usually constantan, but other thermocouple pair materials may be used. We also note that we do not mean to exclude from our scope designs such as in FIG. 3A, but where a plating of metal, such as gold, is put on the surface of the tip and over the junction 4. Such a minor interface does not alter the design feature discussed here. The tip 1a may not be sharpened, but it may be rounded or hemispherical as the application governs. The tip need not be straight either. It may have a permanent hook in it, as is needed in certain procedures, or it could even have a flexible tip portion 1a. Such an electrode is shown in FIG. 3B. In the latter case, the end of shaft 1 may, for example, be a coiled spring 1c which has a permanent arc in it, thus making it flexible. Wire 5 may also be coiled inside 1 to give it flexibility. Such a coiled spring has been reported by Zervas, et. al. and by Radionics, Inc., but, in both cases, these previous designs had an internal thermocouple sensor within the tip. In FIG. 3B, the externalized thermocouple junction 4, where the two thermocouple metals are electrically fused, is part of the external surface of the electrode tip.

Figure 2B:
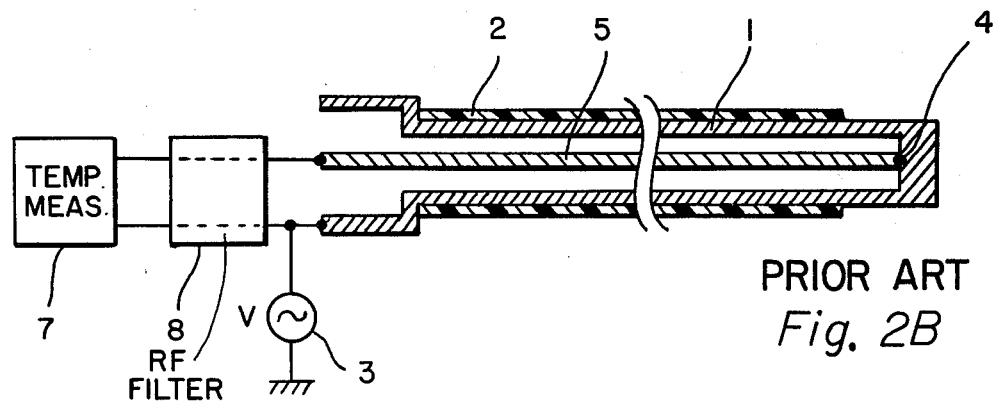

We note in FIG. 3B, that the same thermocouple readout system as shown in FIG. 2B is employed.

Figure 3C:
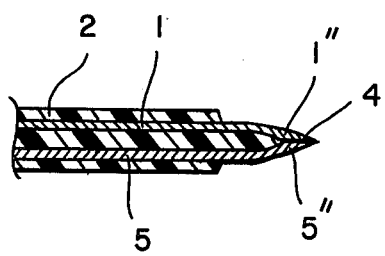

FIG. 3C illustrates a variant of the externalized thermocouple rf electrode tip. In this case, instead of a tube, element 1 is a solid elongated element, perhaps a wire, which runs along side element 5 throughout the length of the electrode. Metals 1 and 5 are fused or electrically bonded at the distal end, forming junction 4. The portions 1" of 1 and 5" of 5 at the distal end of 1 and 5 form the tip of the electrode, and they form a portion of the external surface of the tip also. The junction is thus intimately and integrally associated with the tip and its surface. Insulation 2 may insulate 5 and 1 from each other, and also serve as the coating for the rf electrode itself, except for the exposed surface at the tip. Wires 1 and 5 may be individually insulated and twisted together along the length of the electrode for stability. The point may be sharpened as shown, but may be other shapes as well.

Figure 3E:
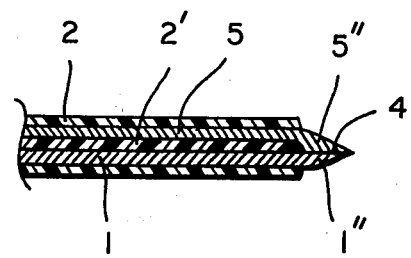
Figure 3D:
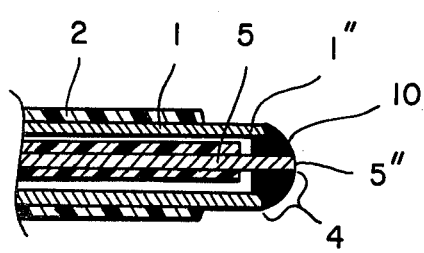

FIG. 3D illustrates a design similar to FIG. 3A involving a tubular metal element 1, but in this case the electrode tip has a blunt, rounded end. The metal wire 5 comes straight out the end 1b of tube 1, and the junction 4 is made by soldering a solder volume 10 between 1" and the tip end 5" of element 5. Again the distal surface of 5" is part of the external surface of the electrode tip, and the solder 10 is also part of the external surface. Thus the junction potential between 5" and 1" is derived from those between 5" and 10 and 10 and 1". Because these junctions are all on the surface of the electrode, we achieve a faithful and rapid representation of adjacent tissue heating. In this case, junction 4 comprises the fusing of 5", 10", and 1", and it is still made between surface-exposed elements.

FIG. 3E shows yet another variant of the externalized thermocouple rf electrode. Element 1 may be a steel wire, providing stiffness and a hard, sharp point. Insulation 2' between 1 and 5 may be a thin coating or microscopic layer. Element 5 may be a thin wire of, say, constantan, and it may be fused to the tip 1" of 1. The portion 5" of 5 which joins to 1" may be a coating of, say, constantan which is ultra thin. The entire tip may be micro-etched to make a point of micron dimension. Such an electrode would be used in neurophysiology to thermally destroy perhaps individual cells with thermal monitoring. This illustrates the very fine gauges of and the smallness of rf electrodes made with the externalized thermocouple junction concept. Thus, such an electrode as in FIG. 3E may be made entirely by a series of insulation and metal electro-depositions or evaporations to yield very uniform and simply constructed thermocouple micro rf lesion electrodes; viz, materials, 1b, 2', 5, and 2 may be entirely built up from substrate depositions, with appropriate maskings, to yield the final electrode. When such an electrodes dimension reaches the micron range, it can be used for recording cellular electrical activity, as well as stimulating the cells electrically and making heat lesions. Thus such an electrode can serve multiple functions which are important in neurophysiology.

Figure 3F:
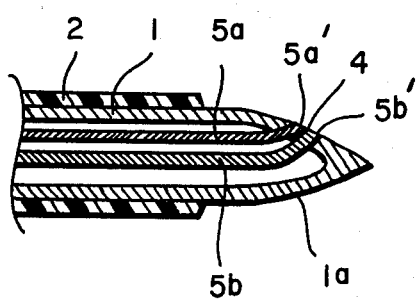

Finally FIG. 3F shows an externalized thermocouple rf electrode wherein the thermocouple wires 5a and 5b are brought up to the electrode tip and are of different material from the shaft 1 or the shaft tip material 1a. This may be done to use, for example, iron and constantan for 5a and 5b, respectively, and stainless steel for shaft 1 and tip 1a. However, the concept of the externalized junction may still apply, as shown in FIG. 3F. Note, that the very distal tip surfaces of 5a and 5b, 5a' and 5b', respectively, are part of the external surface of the electrode tip 1a. The thermocouple junction 4 is between 5a and 5b just near the surface portions 5a' and 5b', and thus 4 is again in intimate thermal contact with the adjacent tissue to be heated by the rf current. One way of implementing such a construction is by drilling a hole in the tip 1a, threading the wires 5a and 5b through the hole, then fusing them together by welding or soldering techniques, and then grinding them flush with the rest of tip 1a. Again, our invention includes the addition of a thin metal coating over the entire tip 1a and junction areas 5a', 5b', and 4, so as to protect these areas from corrosion or other effects. In this sense, we may say that a portion of each of the thermocouple elements near their junction substantially comprises at least a portion of the external surface of the rf lesioning electrode tip.

Having described in detail various embodiments of my invention, it will now be apparent to those skilled in the art that numerous modifications can be made therein without departing from the scope of the invention as defined in the following claims.

What I claim and desire to secure by Letters Patent of the United States is:

1. An electrode adapted for making radio frequency heat lesions in the tissue of the living body and having built-in a thermocouple sensor which can sense the temperature of the bodily tissue which is being heated, the electrode having an elongated shape with a distal end that is intended to be directed at the bodily tissue to be heated and a proximal end having connection means which is adapted to be connected to an external source of radio frequency energy and to an external thermocouple temperature monitoring apparatus, a portion of the elongated portion of said electrode being covered with an insulating material, said electrode having an uninsulated conductive tip at its distal end from which, when in use, radio frequency current will flow to heat surrounding tissue, said electrode comprising conductive means connecting said uninsulated tip to said connection means located near said proximal end of said electrode and adapted for connection to an external source of radio frequency potential whereby when in use said uninsulated tip will be at said radio frequency potential, said electrode comprising a first metal wire element and a second metal wire element, both metal wire elements running from said proximal end to said distal end of said electrode, said two metal elements being the two sides of a thermocouple pair, said two metal elements being electrically insulated from each other over the length of said electrode except at said distal end, the distal ends of said two metal elements being electrically fused at said distal end of said electrode to form a thermocouple junction in such a way that a portion of each of said distal ends of said two metal elements and a portion of said fused junction are part of external surface of said uninsulated tip, the proximal ends of said two metal elements near the proximal end of said electrode are so adapted to be connected through said connection means to an external thermocouple junction potential measuring apparatus; whereby, when in use and when said electrode is inserted into the living body, then the radio frequency potential at said uninsulated tip of said electrode will cause current to flow in, and thus heat up, the tissue surrounding said uninsulated tip, and said distal portions of said two metal elements and said portion of thermocouple junction which are on the external surface of said uninsulated tip will provide intimate thermal contact with the heated tissue adjacent to said external surface, and thus, a reliable measure of the temperature of said adjacent tissue.

2. The electrode of claim 1 wherein said conductive means connecting said uninsulated tip to said connection means, a portion of said uninsulated conductive tip, and said first metal thermocouple element are the same continuous metal structure.

3. The electrode of claim 2 wherein said continuous metal structure comprises a stainless steel tube, a portion of the distal end of said tube being a portion of the external surface of said uninsulated tip, and said second metal thermocouple element being a wire of metal dissimilar from stainless steel which runs the length of said tube and being electrically fused at the distal end portion of said stainless steel tube so that said tube and said wire form a thermocouple junction at the uninsulated tip of said electrode, and a portion of said metal wire near said junction forming at least a portion of the external surface of said uninsulated tip.

4. The electrode of claim 3 wherein said metal wire is located within the lumen of said stainless steel tube and insulated therefrom by an insulating coating except for the point of said thermocouple junction at said uninsulated tip.

5. The electrode of claim 4 wherein said metal wire is made of constantan.

6. A radio frequency heat lesion electrode with thermocouple sensor in its tip to monitor lesion temperature and adapted for being inserted into and for making heat lesions in the tissue of the spinal cord, the electrode having a distal end and a proximal end and comprising a stainless steel tubular shaft having a corresponding distal end and a corresponding proximal end, the tubular shaft being covered with an insulating material over the portion of length of said shaft adjacent to which no tissue heating is desired, said shaft having an uninsulated portion at its distal end adjacent to which tissue heating is desired, a metal wire of material dissimilar to stainless steel which is located inside of said tubular shaft, the metal wire and said shaft being insulated from each other except at the distal end of each at which location said metal wire and said shaft are electrically fused together to form a thermocouple temperature sensing junction, said electrode having a sharpened uninsulated tip at its distal end adapted to pierce and penetrate the spinal cord, the uninsulated tip being so constructed that at least a portion of said tubular shaft and at least a portion of said metal wire and at least a portion of fused junction are at the external surface of said uninsulated tip so that said thermocouple sensor is in close thermal contact with tissue to be heated adjacent to said uninsulated tip, said electrode having means at its proximal end to connect said tubular shaft to an external source of radio frequency potential and to connect said metal wire and said tubular shaft to external apparatus to measure the thermocouple potential arising from said thermocouple junction; whereby, when in use and when said electrode tip is inserted into tissue of the spinal cord, said tissue can be heated by the current arising from said radio frequency potential at said uninsulated tip, and the temperature of the heated tissue in close proximity to said uninsulated tip can be reliably monitored.

* * * * *